(12) United States Patent
Giles

(10) Patent No.: US 6,518,432 B1
(45) Date of Patent: Feb. 11, 2003

(54) PROCESS

(75) Inventor: Melvyn E. Giles, Barrow-upon-Soar, Leics. (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/555,050

(22) PCT Filed: Apr. 14, 2000

(86) PCT No.: PCT/SE00/00713

§ 371 (c)(1),
(2), (4) Date: May 24, 2001

(87) PCT Pub. No.: WO00/63175

PCT Pub. Date: Oct. 26, 2000

(30) Foreign Application Priority Data

Apr. 15, 1999 (SE) .............................................. 9901340

(51) Int. Cl.[7] .......................................... C07D 213/127
(52) U.S. Cl. ........................ 546/329; 546/304; 546/329; 514/357

(58) Field of Search ................................. 546/304, 329; 514/255

(56) References Cited

U.S. PATENT DOCUMENTS

| | | | | |
|---|---|---|---|---|
| 5,455,259 A | * | 10/1995 | Griffith et al. | ............... 514/357 |
| 5,607,935 A | * | 3/1997 | Griffith et al. | ............... 514/255 |

FOREIGN PATENT DOCUMENTS

| | | |
|---|---|---|
| EP | 0 691 957 B1 | 8/1997 |
| EP | 0 633 879 B1 | 11/1998 |
| WO | 94/22831 | 10/1994 |

* cited by examiner

*Primary Examiner*—Alan L. Rotman
*Assistant Examiner*—Janet Coppins
(74) *Attorney, Agent, or Firm*—Nixon & Vanderhye

(57) ABSTRACT

The invention relates to a novel process for the preparation of certain pharmaceutically active pyridyl compounds.

4 Claims, No Drawings

PROCESS

The present invention relates to an improved process for the preparation of certain medicinal agents.

EP 0 633 879 B 1 discloses compounds said to have NMDA receptor antagonist activity. The compound known as (S)-1-phenyl-2-(2-pyridyl)ethanamine is of particular interest, especially for the treatment of stroke. However, the processes disclosed in EP 0 633 879 B 1 for the preparation of this compound suffer from certain disadvantages, for example, requiring the use of butyl lithium which is not convenient to use on a large scale.

A new process for the preparation of (S)-1-phenyl-2-(2-pyridyl)ethanamine has now been developed which avoids the need to use butyl lithium and is therefore more suitable for commercial use. Since the process of the invention eliminates the need to use butyl lithium it therefore also has the additional advantage that it does not suffer from environmental problems associated with butane emission. Further, it has surprisingly been found that the process of the invention can be carried out with only a catalytic amount of base [with respect to the 2-picoline of formula (II)] rather than a stoichiometric amount of base as used in EP 0 633 879 B 1. Overall the claimed process is therefore more efficient, safer, more environmentally friendly and cheaper than that of EP 0 633 879 B 1.

In a first aspect the invention therefore provides a process for the preparation of a compound of formula (I) or a pharmaceutically acceptable salt thereof:

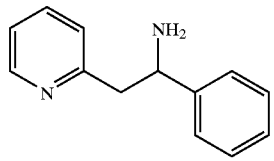

(I)

which comprises:
reaction of a compound of formula (II):

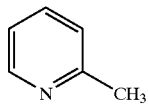

(II)

with a compound of formula (III)

(III)

in the presence of a metal hexamethyldisilazide and optionally thereafter resolving the enantiomers of compound (I) and forming a pharmaceutically acceptable salt.

A compound of formula (III) can be prepared from benzaldehyde and a metal hexamethyldisilazide, preferably lithium hexamethyldisilazide (LHMDS). Preferably the compound of formula (III) is prepared at a reduced temperature, that is, below 35° C. and preferably below 25° C.

The reaction of compounds (II) and (III) is suitably carried out at elevated temperature, for example, at about 40° C. The reaction can be carried out in an inert solvent, preferably in an ethereal solvent such as t-butyl methyl ether or more preferably tetrahydrofuran. Preferably the metal hexamethyldisilazide is lithium hexamethyldisilazide (LHMDS) and this base is used in a catalytic amount with respect to the 2-picoline (2-methylpyridine) of formula (II), for example, about 10 mol %. Acidic work-up of the reaction mixture gives the required compound of formula (I).

Compounds of the invention can form pharmaceutically acceptable solvates and salts. The compounds of the formula (I) can form acid addition salts with acids, such as conventional pharmaceutically acceptable acids, for example, malic, hydrochloric, hydrobromic, phosphoric, acetic, fumaric, salicylic, citric, lactic, mandelic, tartaric, trifluoroacetic and methanesulphonic acids. Preferred salts are the malate and hydrochloride salts.

Particularly preferred salts are those which can be prepared using chiral acids to give salts of a single enantiomer of compound (I) as disclosed in EP 0 691 957 B 1. Preferably the racemic compound of formula (I) is treated with (S)-malic acid to give (S)-1-phenyl-2-(2-pyridyl)ethanamine (S)-malate.

In a further aspect the invention provides (S)-1-phenyl-2-(2-pyridyl)ethanamine and salts thereof, particularly the (S)-malate salt, when prepared using the processes described herein.

The invention is illustrated by the following example.

EXAMPLE

(S)-α-Phenyl-2-pyridineethanamine (S)-malate

A solution of lithium hexamethyldisilazide (1100 ml of a 1.0M solution in tetrahydrofuran, 1.1 mol) was added dropwise under nitrogen with cooling to a stirred solution of benzaldehyde (102 ml, 1.0 mol) in tetrahydrofuran (305 ml) whilst maintaining the temperature below 25° C. The resulting solution was allowed to stir at 20° C. for 30 minutes prior to the addition of 2-picoline (101 ml, 1.0 mol) in one portion followed by further tetrahydrofuran (102 ml). The reaction mixture was then heated to 40° C. over 30 minutes and then maintained at 40° C. for 90 minutes. The solution was then cooled to 20° C. over 10 minutes and added dropwise to a solution of conc. hydrochloric acid (420 ml, 5.0 mol) in demineralised water (900 ml) with cooling so as to maintain the temperature between 10 and 20° C. The resulting mixture (pH 1) was allowed to stir 20° C. for 15 minutes and then the layers were separated. The lower aqueous phase was separated and washed with ethyl acetate (2×900 ml), then basified by the addition of a solution of sodium hydroxide (200 g, 5.0 mol) in demineralised water (830 ml) with cooling so as to maintain the temperature in the range 10 to 20° C. The resulting mixture (pH 12) was then stirred at 20° C. for 15 minutes, then extracted with ethyl acetate (2×800 ml). The ethyl acetate solution was then added to a solution of S-malic acid (120.7 g. 0.9 mol) in ethanol (1060 ml), followed by the addition of a seed of the title compound (0.2 g). This mixture was stirred for 30 minutes at 20° C., then cooled to 0° C. and stirred for 20 hours at 0° C. The suspension was filtered and washed with ethanol (530 ml) to give a white solid which was dried in a vacuum oven at 40° C. overnight to give (S)-α-phenyl-2-pyridineethanamine (S)-malate (119.07 g, 35.8%) as a white solid, identical to known material.

What is claimed is:

1. A process for the preparation of a compound of formula (I) or a pharmaceutically acceptable salt thereof:

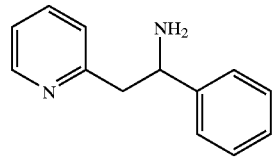
(I)

which comprises:

reaction of a compound of formula (II):

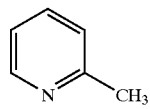
(II)

with a compound of formula (III):

(III)

in the presence of a metal hexamethyldisilazide and optionally thereafter resolving the enantiomers of compound (I) and forming a pharmaceutically acceptable salt, wherein the metal hexamethyldisilazide is used in a catalytic amount with respect to the compound of formula (II).

2. A process according to claim 1 in which the metal hexamethyldisilazide is lithium hexamethyldisilazide.

3. A process according to claim 1 in which compounds (II) and (III) are reacted in an ethereal solvent.

4. A process according to claim 1 in which the molar ratio of compound (II) to lithium hexamethyldisilazide is about 10:1.

* * * * *